United States Patent
Gutmann et al.

[19]

[11] Patent Number: 6,150,570
[45] Date of Patent: Nov. 21, 2000

[54] METHOD OF PRODUCING CRYSTALLINE D-SORBITOL

[75] Inventors: Pedro Gutmann, Kronberg; Jakob Wiesenbart, Göppingen, both of Germany

[73] Assignee: Metallgesellschaft AG, Frankfurt, Germany

[21] Appl. No.: 09/230,159

[22] PCT Filed: Jul. 21, 1997

[86] PCT No.: PCT/EP97/03924

§ 371 Date: Apr. 19, 1999

§ 102(e) Date: Apr. 19, 1999

[87] PCT Pub. No.: WO98/03457

PCT Pub. Date: Jan. 29, 1998

[30] Foreign Application Priority Data

Jul. 23, 1996 [DE] Germany .......................... 196 29 640

[51] Int. Cl.[7] .................................................. C07C 27/26
[52] U.S. Cl. .......................................... 568/868; 568/852
[58] Field of Search ..................... 568/852, 868

[56] References Cited

U.S. PATENT DOCUMENTS

| | | | |
|---|---|---|---|
| 1,724,627 | 8/1929 | Varnau et al. ............. | 127/16 |
| 2,315,699 | 4/1943 | Goepp ..................... | 568/868 |
| 2,594,863 | 4/1952 | Buck et al. ............... | 568/868 |
| 3,330,874 | 7/1967 | Shannon .................. | 568/868 |
| 4,293,570 | 10/1981 | Vadasz .................... | 426/3 |
| 4,605,794 | 8/1986 | Reiff et al. .............. | 568/852 |
| 5,068,467 | 11/1991 | Kunimi et al. ............ | 568/852 |

OTHER PUBLICATIONS

Kirk–Othmer, Encyclopedia of Chemical Technology, evaporation, 3rd, vol. 9, pp. 478–481, Apr. 1980.

*Primary Examiner*—Gary Geist
*Assistant Examiner*—Taylor V. Oh
*Attorney, Agent, or Firm*—Michael J. Striker

[57] ABSTRACT

The continuous process for making crystalline D-sorbitol using a melt crystallizer consisting of a cooled container and a horizontally arranged rotatable shaft equipped with disk elements and mixing parts to form a worm includes evaporating an aqueous D-sorbitol solution at 5 to 200 mbar and at a temperature of 130° to 170° C. in vacuum, advantageously in a thin film evaporator, to obtain a D-sorbitol melt containing less than 0.5 % by weight water; cooling the D-sorbitol melt to a temperature of 5 to 15° C. above a solidification point of the D-sorbitol melt; melt crystallizing the D-sorbitol melt obtained during the evaporating in the melt crystallizer with an average dwell time of 1 to 5 hours to form D-sorbitol crystals and grinding and sieving the D-sorbitol crystals formed during the melt crystallizing of step d) to form a D-sorbitol end product containing more than 90% by weight of a γ modification of crystalline D-sorbitol. During the process no solid D-sorbitol is added to the D-sorbitol melt in order to form initial crystallization nuclei for crystallization and no subsequent maturation steps of the end product are included in the process.

7 Claims, 1 Drawing Sheet

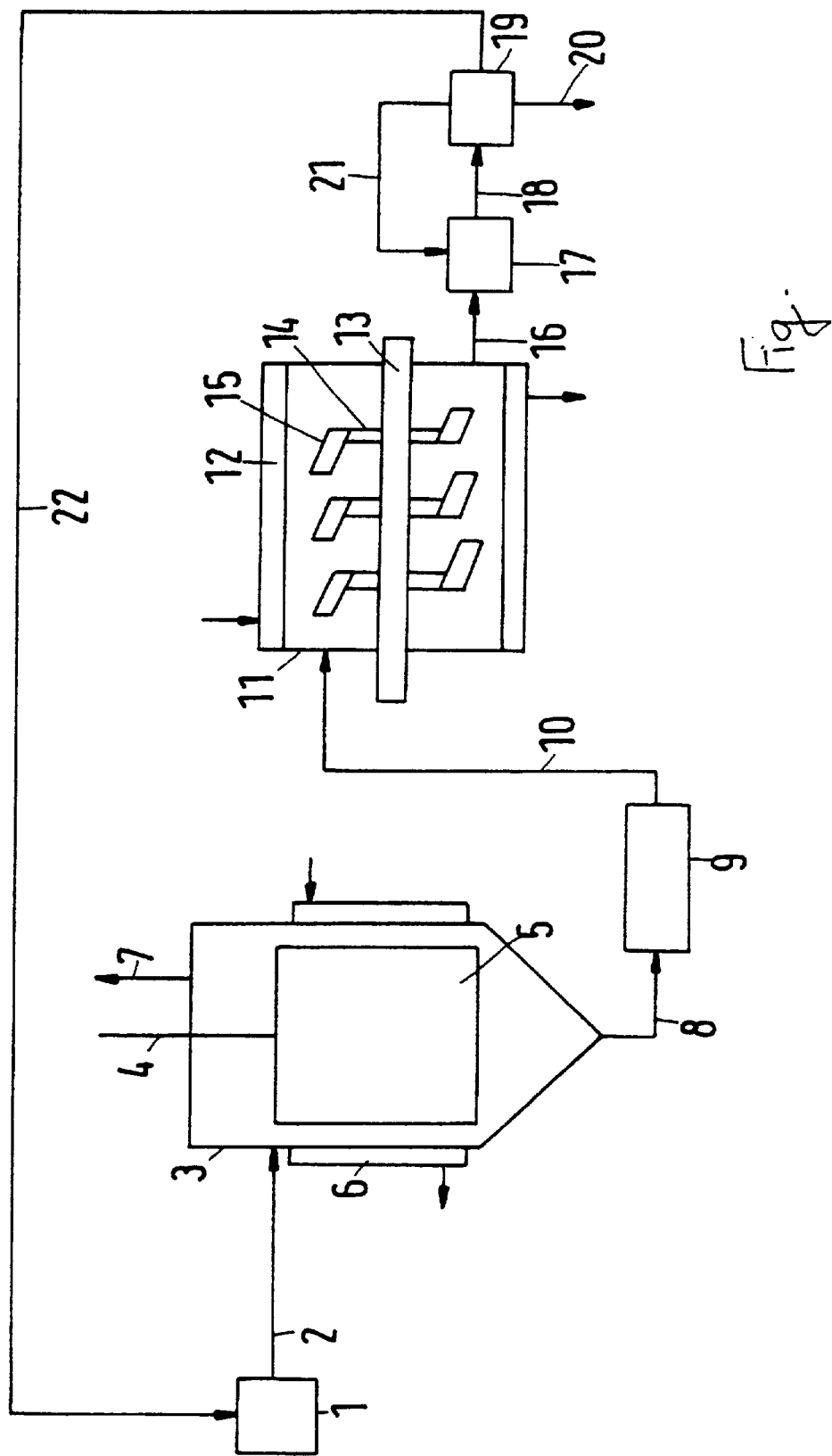

METHOD OF PRODUCING CRYSTALLINE D-SORBITOL

BACKGROUND OF THE INVENTION

1. Field of the Invention

This invention relates to a process of producing crystalline D-sorbitol through evaporation of an aqueous D-sorbitol solution in a vacuum and subsequent melt crystallization of the D-sorbitol melt obtained during the evaporation.

2. Prior Art

D-sorbitol belongs to the hexahydric alcohols and has the empirical formula $C_6H_{14}O_6$. D-sorbitol is made from D-glucose through electrolytic reduction or catalytic hydrogenation. D-sorbitol has a sweet taste and is used as sugar substitute, and it is also used in the cosmetic and pharmaceutical industries and for the production of polyethers and surfactants. D-sorbitol crystallizes in the α-, β- and γ-modification, where the γ-modification is the thermodynamically stable form. D-sorbitol is used either in the form of concentrated aqueous solutions or in solid, crystalline form as industrial raw material. To ensure an easy handling of the solid crystalline D-sorbitol, it is desired that it should largely be present in the γ-modification, as this form is not only thermodynamically stable, but also comparatively little hygroscopic.

From the DE-A 32 45 170 there is known a process of producing sorbitol with improved pelletizing properties, where a solution of crystallized glucose hydrogenates at a temperature below 170° C., and the sorbitol solution thus obtained is spray-dried at a temperature in the range from 140 to 170° C., so that the product obtained has a water content of less than 1%.

From the DE-C 23 50 619 there is known a process of continuously producing crystallized sorbitol by introducing molten and granular sorbitol in a container, in which the mass thus obtained is kept in movement at an elevated temperature. In this process, atomized sorbitol or sorbitol in the form of droplets, sheets, mists or strips with more than 90% dry matter is continuously introduced in the container in the molten condition together with 20 to 80 wt-% sorbitol powder with a grain size below 5 mm, and the mass thus obtained is agitated by rotating the open container with a horizontal axis or an axis inclined towards the horizontal, where molten sorbitol or sorbitol powder is applied onto the surface of the agitated mass. The agitated mass is maintained at a temperature of more than 90° C., and the larger grains precipitating chiefly on the surface of the agitated mass are trapped at the outlet of the rotating container due to overflow and are subsequently subjected to a maturing stage for crystallizing the sorbitol. Before the melt crystallization there is provided a vessel for the vacuum evaporation, which is suited to bring a sorbitol solution to a dry content of more than 98 wt-%.

The DE-A 37 32 141 outlines the known processes of producing solid sorbitol. In one of these processes the sorbitol solution is evaporated in a vacuum until an almost anhydrous melt is obtained. Upon cooling, possibly by adding crystalline sorbitol, the melt solidifies, and from the solidified melt granular dust-like sorbitol is obtained by crushing and grinding. However, the product thus produced has a very wide range of particle sizes, and the content of γ-sorbitol is subject to large fluctuations. In addition to crystalline sorbitol, considerable amounts of amorphous sorbitol are contained. This results in poor free-flowing properties, and during storage the product agglomerates to form a hard mass. In accordance with a further known process, a concentrated sorbitol solution is dripped or coarsely sprayed onto a mechanically moving bed of crystallized sorbitol. The moving and wetted crystal bed is maintained at a temperature of 60 to 80° C. for vaporizing the water by passing air or an inert gas therethrough. After a corresponding crystallization period, part of the solid sorbitol is continuously withdrawn while the same is cooled. The product thus obtained likewise has a very wide range of particle sizes. It is also disadvantageous that the individual sorbitol particles quickly agglomerate to form hard masses as they absorb little moisture from the air, and that the dissolution period in water is relatively long. Finally, there is known a further process, where a 50 to 80% purified sorbitol solution is continuously split into extremely fine droplets by means of a spraying device, and at the same time finely divided crystalline sorbitol together with air is introduced in a spray tower such that the sprayed sorbitol solution covers the crystalline sorbitol particles with a thin film. For the vaporization of water there is additionally blown in a stream of hot air. The residual moisture can be varied within relatively wide limits by the temperature of the hot air and the ratio between the hot air and the sorbitol solution. After a crystallization period of 20 to 90 minutes, the dry product is cooled to a temperature <40° C., and part of the product is withdrawn, while the other part is recirculated to the spray tower. Even the handling properties of the crystalline sorbitol produced in accordance with this process are not satisfactory in the final analysis. To eliminate the disadvantages of the products produced in accordance with the known processes, the DE-A 37 32 141 proposes a process of producing crystalline sorbitol with improved handling properties, which operates according to the principle of spray drying, where a 50 to 80% aqueous sorbitol solution and crystalline sorbitol are supplied to the spray drier.

SUMMARY OF THE INVENTION

It is the object underlying the invention to create a process of producing crystalline D-sorbitol, which operates according to the principle of melt crystallization, but eliminates the known disadvantages of melt crystallization. The crystalline D-sorbitol produced in accordance with the invention should have a melting point of 98 to 100° C., a water content <0.5 wt-%, and a content of γ-modification >90%. Such product has optimum handling properties when it is used as industrial raw material. Therefore, the production process, which operates according to the principle of melt crystallization with preceding vacuum evaporation, should be developed or improved such that the requirements as to product quality are maintained safely and reliably over an extended operating period, which in addition requires an economic operation.

The object underlying the invention is solved in that a D-sorbitol melt with a water content <0.5 wt-% and a temperature which is 5 to 15° C. above the solidification point of the melt is crystallized in a melt crystallizer, which consists of a cooled container and a horizontally arranged, rotatable shaft equipped with disk elements and mixing bars, which disk elements and/or mixing bars are arranged on the shaft in the form of a worm, and where the disk elements, the mixing bars and/or the shaft are cooled, and in that the crystals withdrawn from the melt crystallizer are processed by grinding and sieving to obtain an end product which consists of more than 90% crystalline D-sorbitol of the γ-modification.

Due to the inventive melt crystallization, it is no longer necessary to add solid D-sorbitol to the D-sorbitol melt, as with the inventive configuration of the melt crystallization a sufficient amount of crystallization nuclei are formed. Due to the relatively high input of mechanical energy, which is effected by the mixing elements to be used in accordance with the invention, crystals with a small average particle size are produced, in which only a very small amount of the melt is included, so that the end product is not noticeably contaminated by amorphous D-sorbitol. In the process in accordance with the invention, a subsequent maturation of the product, i.e. the conversion of amorphous D-sorbitol or D-sorbitol present in the α- or β-modification into the γ-modification, can therefore advantageously be omitted. Furthermore, the inventive melt crystallization advantageously leads to the fact that the effort for the grinding operation can be kept low. Finally, due to the cooling of the individual parts of the melt crystallizer provided in accordance with the invention, a very favorable course of the melt crystallization is achieved, which leads to the fact that the end product has a content of γ-modification >90%, so that the subsequent maturation of the product can be omitted.

In accordance with the invention it has turned out to be particularly advantageous to convert an aqueous solution with a D-sorbitol content of 60 to 80 wt-% into a D-sorbitol melt with a water content <0.5 wt-% through evaporation at 5 to 200 mbar, preferably 50 to 200 mbar, and a temperature of 130 to 170° C., preferably 130 to 140° C., and to cool the D-sorbitol melt to a temperature which is 5 to 15° C., preferably 10 to 15° C., above the solidification point of the melt. By means of the inventive evaporation a considerable dehydration is achieved, so that relatively little effort is advantageously required for cooling the D-sorbitol melt.

In accordance with the invention it has furthermore turned out to be particularly advantageous to effect the evaporation of the aqueous D-sorbitol solution in a thin-film evaporator, as in this apparatus the evaporation conditions can be maintained very precisely, and the dehydration is achieved within a relatively short period.

In accordance with a further aspect of the invention the D-sorbitol melt is cooled to a temperature in the range from 105 to 115° C., the D-sorbitol melt has an average dwell time of 1 to 5 hours in the melt crystallizer, and the crystals withdrawn from the melt crystallizer have an average particle diameter $d_{50}$ of <2 mm. Under these process conditions, an end product of high quality can safely be produced.

In accordance with the invention it is finally provided that the process is performed continuously, which has a particularly advantageous effect on its efficiency. The required operating safety of the continuous process in accordance with the invention is reliably maintained.

BRIEF DESCRIPTION OF THE DRAWING

The objects, features and advantages of the invention will now be illustrated in more detail with the aid of the following description of the preferred embodiment, with reference to the accompanying drawing, in which the sole FIGURE is a flow chart of one embodiment of a process for producing crystalline D-sorbitol according to the invention.

DESCRIPTION OF THE PREFERRED EMBODIMENT

A reservoir 1 contains an aqueous D-sorbitol solution with a D-sorbitol content of about 70 wt-%. Such solutions are commercially available. D-sorbitol is produced through catalytic hydrogenation of D-glucose in an aqueous solution. After the production of D-sorbitol, the aqueous solution is purified and concentrated to a D-sorbitol content of about 70 wt-%. The reservoir 1 is provided with a stirrer not represented in the drawing.

Via line 2, the aqueous D-sorbitol solution is continuously supplied to the thin-film evaporator 3, which is equipped with a stirrer 4 provided with one or more wiper blades 5. The aqueous D-sorbitol solution trickles in a thin film down the wall of the thin-film evaporator 3 and is heated to a temperature of about 135° C. by the heating medium circulating in the heating jacket 6. In the thin-film evaporator 3, water is removed from the aqueous D-sorbitol solution to a residual content <0.5 wt-%. The evaporation of the water takes place at about 100 mbar, and the steam is discharged from the thin-film evaporator 3 via line 7. The D-sorbitol melt produced in the thin-film evaporator 3 is removed continuously from the wall of the thin-film evaporator 3 by the wiper blades 5 and continuously flows from the lower part of the thin-film evaporator 3 via line 8 at a temperature of about 135° C. to the cooler 9, where it is cooled to a temperature of about 110 to 115° C. Under these conditions, the D-sorbitol melt has good flow properties, so that the continuous operation is not impeded. The D-sorbitol melt flowing in line 8 is adjusted to normal pressure, so that the cooler 9 operates at normal pressure.

Via line 10, the cooled D-sorbitol melt with a temperature of 110 to 115° C. is introduced continuously into the melt crystallizer 11. The melt crystallizer 11 is designed as cylindrical container, and it has a cooling jacket 12 through which heat is dissipated via a cooling medium. In addition, the melt crystallizer 11 is provided with a rotatable shaft 13, on which there are mounted disk elements 14 and mixing bars 15. A cooling medium flows both through the shaft 13 and through the disk elements 14 and the mixing bars 15, so that heat is dissipated from the melt crystallizer 11 also through these components. The mixing bars 15 are arranged on the disk elements 14 in the form of a worm, so that the radial mixing effect caused by the disk elements 14 is superimposed by an axial transport effect caused by the mixing bars 15. In addition, the disk elements 14 and the mixing bars 15 provide for a comminution of the crystal agglomerates formed in the melt crystallizer 11. In the front zone of the melt crystallizer 11 the D-sorbitol melt is converted into a plastilina-like mass. In the middle zone of the melt crystallizer 11, the cooler and already more solid D-sorbitol mass is crushed by the input of mechanical energy effected by the mixing elements. In the rear zone of the melt crystallizer 11, the crushed mass is further comminuted, and there is in addition produced an internal circulation of part of the crystalline D-sorbitol formed in the middle and front zone of the melt crystallizer 11. The powdery crystalline D-sorbitol is discharged from the melt crystallizer 11 via a laterally arranged port, in which a vertically adjustable weir is provided for controlling the amount of D-sorbitol present in the melt crystallizer 11. The crystalline D-sorbitol leaves the melt crystallizer 11 at a temperature of 40 to 60° C. In particular the mixing bars 15 are responsible for preventing caking in the melt crystallizer 11.

The crystalline D-sorbitol is delivered via line 16 to the mill 17, where the product is ground. However, there is relatively little grinding operation, as the crystalline D-sorbitol always leaves the melt crystallizer 11 with an average particle diameter $d_{50}$ of <2 mm, but in general with an average particle diameter $d_{50}$ of <1 mm. The ground product is supplied via line 18 to a sieve 19, from which the end product with the respectively required range of particle sizes is withdrawn via line 20. The oversize fraction is recirculated to the mill 17 via line 21, whereas the undersize fraction is supplied via line 22 to the reservoir 1, where it is dissolved in the aqueous D-sorbitol solution by stirring.

The end product discharged via line 20 has a melting point of about 98 to 100° C., a water content of <0.5 wt-%, and a content of γ-modification >90%, where in general the content of γ-modification is about 95%. The crystalline D-sorbitol produced by the process in accordance with the invention has good handling properties, as it has a good free-flowing property, and during storage the individual crystals do not agglutinate.

What is claimed is:

1. A continuous process for making crystalline D-sorbitol, said process comprising the steps of:
   a) providing a melt crystallizer consisting of a cooled container and a horizontally arranged rotatable shaft equipped with disk elements and mixing parts, said disk elements and/or mixing bars being arranged on said shaft to form a worm;
   b) evaporating an aqueous D-sorbitol solution at 5 to 200 mbar and at a temperature of 130° to 170° C. in vacuum to obtain a D-sorbitol melt containing less than 0.5% by weight water;
   c) cooling said D-sorbitol melt to a temperature of 5 to 15° C. above a solidification point of said D-sorbitol melt;
   d) melt crystallizing said D-sorbitol melt obtained during said evaporating of step b) in said melt crystallizer with an average dwell time of 1 to 5 hours to form D-sorbitol crystals; and
   e) grinding and sieving said D-sorbitol crystals formed during the melt crystallizing of step d) to form a D-sorbitol end product containing more than 90 % by weight of a γ modification of crystalline D-sorbitol;
   wherein no solid D-sorbitol is added to said D-sorbitol melt in order to form initial crystallization nuclei for crystallization and no subsequent maturation steps of the end product are included in the process.

2. The continuous process as defined in claim 1, wherein said aqueous D-sorbitol solution contains from 60 to 80% water.

3. The continuous process as defined in claim 1, wherein said temperature at which said evaporating takes place is from 130° to 140° C. and said temperature at which said cooling takes places is from 10 to 15° C. above said solidification point of said D-sorbitol melt.

4. The continuous process as defined in claim 1, wherein said evaporating takes place in a thin-film evaporator.

5. The continuous process as defined in claim 1, wherein said temperature at which said cooling takes places is from 105 to 115° C.

6. The continuous process as defined in claim 1, further comprising removing said D-sorbitol crystals from the melt crystallizer and wherein said D-sorbitol crystals so removed have an average particle diameter $d_{50}$ of less than 2 mm.

7. The continuous process as defined in claim 1, further comprising inputting mechanical energy into said melt in said melt crystallizer by means of the mixing elements and cooling said disk elements, said mixing bars and/or said shaft of said melt crystallizer during the melt crystallizing.

* * * * *